United States Patent [19]
Reger

[11] Patent Number: 5,469,868
[45] Date of Patent: Nov. 28, 1995

[54] METHOD OF MAKING AN ARTIFICIAL HEART VALVE STENT

[75] Inventor: Vincent A. Reger, Portland, Oreg.

[73] Assignee: Reger Medical Inc., Portland, Oreg.

[21] Appl. No.: 286,162

[22] Filed: Aug. 4, 1994

Related U.S. Application Data

[63] Continuation of Ser. No. 84,663, Jun. 28, 1993, abandoned, which is a continuation of Ser. No. 834,416, Feb. 12, 1992, Pat. No. 5,258,023.

[51] Int. Cl.$^6$ ............................... A61B 19/00; A61F 2/24
[52] U.S. Cl. ............................... 128/898; 623/2; 623/66; 623/901
[58] Field of Search .................................. 623/2, 11, 66, 623/901, 12; 128/898; 112/262.1; 29/890.12, 890.124, 890.126, 890, 128, 890.132

[56] References Cited

U.S. PATENT DOCUMENTS

| | | | |
|---|---|---|---|
| 3,466,671 | 9/1969 | Siposs | 623/2 |
| 4,106,129 | 8/1978 | Carpentier et al. | 623/2 |
| 4,626,255 | 12/1986 | Reichart et al. | 623/2 |
| 4,680,031 | 7/1987 | Alonso | 623/2 |
| 5,163,954 | 11/1992 | Curio et al. | 623/2 |
| 5,258,023 | 11/1993 | Reger | 623/2 |

*Primary Examiner*—Paul B. Prebilic
*Attorney, Agent, or Firm*—Foster & Foster; Lynn G. Foster

[57] ABSTRACT

A novel, long lasting prosthetic heart valve compatible with implantation in a human natural heart valve annulus. The prosthetic heart valve comprises a trileaflet heart valve apparatus which in form, dimension, and function resembles a human trileaflet heart valve, but which is formed of synthetic resinous material. A seamless supporting frame capable of annular deformation and limited perimetric expansion during each heartbeat is totally enveloped in an essentially biologically inert cylindrical cover to form a cusp supporting stent for the valve leaflet apparatus. The free top and bottom edges of the cylindrical cover are disposed on the exterior of the stent and everted outward to provide at least one sewing ring. Valve embodiments comprise aortic and mitral implantable valves. For the aortic implant, the outwardly everting free sewing ring forming edges are separated by circumferentially disposed compressible and expandable material which provides a pliable, compliant interface between the valve and the natural valve annulus at the implanting site. In one embodiment, the synthetic trileaflet heart valve apparatus is formed by a unicast mold. In another embodiment, the heart valve apparatus is formed from a cylinder of synthetic resinous material. Valve sewing ring covers can be selectively impregnated with antibiotic medicants to substantially eliminate early post implant infection. Use of non-thrombogenic biochemically inert materials in a valve apparatus which mimics operation of a natural heart valve essentially eliminates the need for long term administration of anticoagulants.

3 Claims, 5 Drawing Sheets

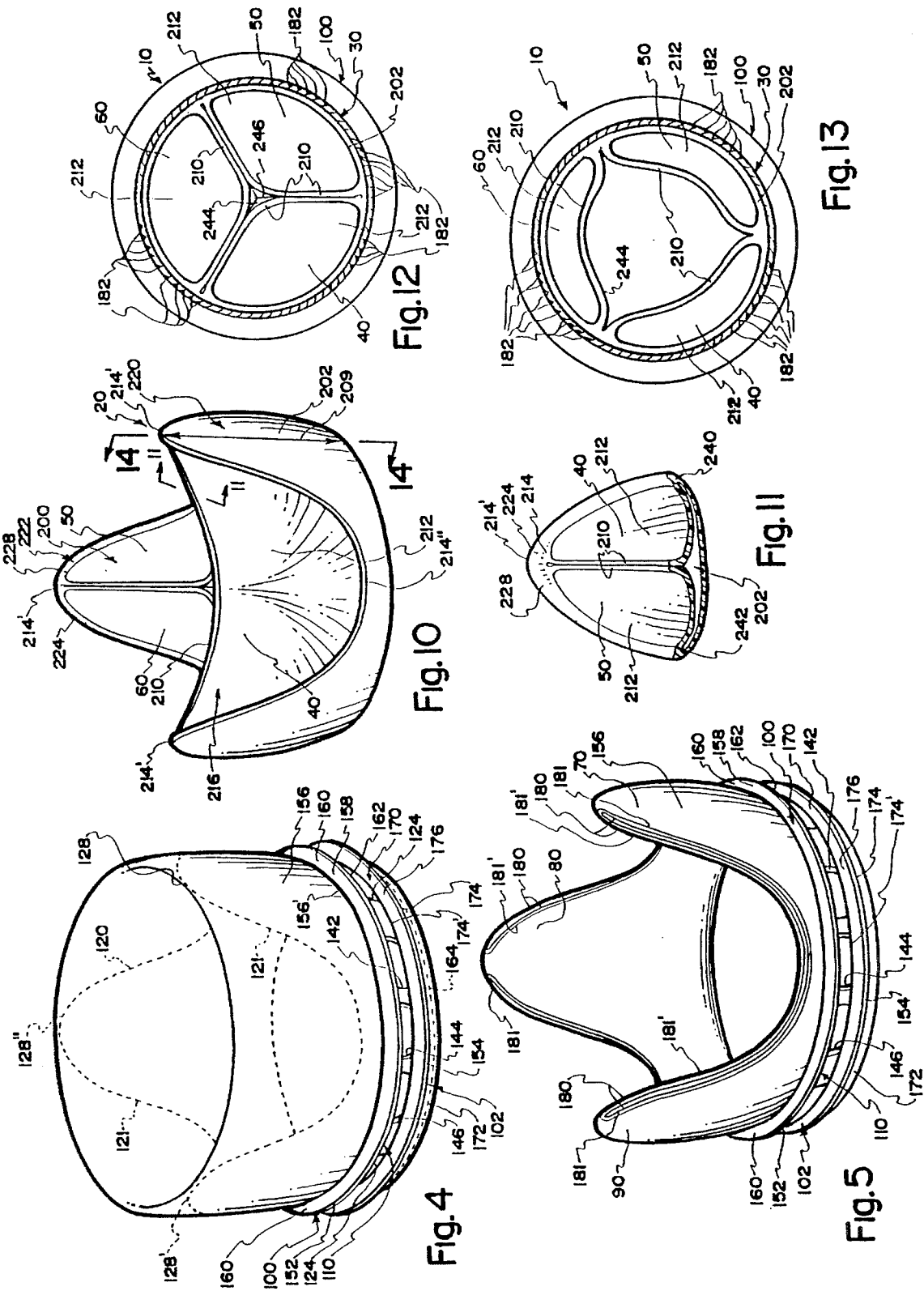

5,469,868

METHOD OF MAKING AN ARTIFICIAL HEART VALVE STENT

CONTINUITY

This application is a continuation of my U.S. patent application Ser. No. 08/084,663, filed Jun. 28, 1993, now abandoned, which is a continuation of U.S. patent application Ser. No. 07/834,416, filed Feb. 12, 1992, now U.S. Pat. No. 5,258,023.

FIELD OF INVENTION

This invention relates to implantable heart valves and in particular to long-lasting implantable prosthetic heart valves comprising valve leaflets made from synthetic materials.

BACKGROUND AND DESCRIPTION OF RELATED ART

Two types of replacement heart valve prostheses are generally known in the art. A first replacement type comprises totally mechanical heart valves which effect unidirectional blood flow through the use of a device using a mechanical closure. The more common mechanical heart valves comprise pressure responsive, pressure directed movement of a ball in a cage or tilting or caged discs.

Examples of pressure responsive, pressure directed ball movement devices are found in U.S. Pat. Nos. 3,263,239, 3,365,728, 3,466,671, 3,509,582, 3,534,410, and 3,723,996. Earliest valve designs were strictly concerned with providing a one-way valve which could be used as a replacement for natural mitral and aortic valves. The earliest known artificial caged ball prothesis was first successfully used for treatment of cardiac valve disease in 1953. With improvements in valves and medical procedures, caged valve prosthesis rapidly became commonplace in the early 1960's.

A source of historical and background information in Mechanical Valve Prostheses is found in The Fourth Edition of Thoracic and Cardiovascular Surgery, published in 1983 by Appleton-Century-Crofts, a publishing division of Prentice-Hall, inc. The earliest caged ball valves comprised stainless steel outflow orifice and rib cages and silicone rubbber poppers. Such valves experienced a high incidence of thromboembolism associated with the outflow orifices and rib cages. The silicone rubber poppers after a period of use often became grossly deformed with resulting incompetence.

To slow the degeneration of the silicone rubber poppers, cloth and plastic coverings were provided for the metal parts. Such coverings resulted in effects of wear and tissue growth in the coverings. The tissue growth, especially in the coverings over struts of the cages led to a thickening of the struts which slowed or stopped ball movement. Fibrous growth across the orifice of the valve led to severe valvular stenosis.

The use of hollow metal spheres and metal tracks in later models of the caged ball rib valves have overcome some of the original problems, and improvements continue to be made to make caged rib ball valve safer and more efficacious.

However, problems inherent with the geometry of the caged ball valve also leads to physiological problems with the use of the valve as a heart valve replacement prosthesis. The caged rib ball valve comprises three orifices through which blood must flow. The primary orifice is the orifice through which blood passes from the effluent chamber being valved. From the primary orifice the blood passes through a secondary orifice defined by the cage and ball, the size of which is determined by the height of the cage and diameter of the ball. The third orifice is the hollow cylindrical path between the ball and cage and the surrounding influent chamber into which the blood flows from the effluent chamber.

The three orifice pattern in a caged ball valve requires sometimes difficult tradeoffs to be made in design. For example, when the ball is large, the third orifice is relatively smaller leading to third orifice stenosis. When the ball is small, the primary orifice is small and relatively stenotic. Further, if travel of the ball in the cage is restricted, as may be required by physiological free space in either the ascending aorta or left ventricle of a patient, the second orifice size must be reduced with resulting relative stenosis thereat. For these reasons, even in a caged ball valve without physiological or structural complications, use is restricted by the inherent three orifice geometry.

Disc valves have been made in the form of caged disc valves and tilting disc valves. Disc valves are generally preferred over caged ball valves because of the inherent low profile configuration of the disk valve. One of the major problems with disc valves and in particular with caged disc valves, is thrombogenicity. Other problems comprise obstructive characteristics inherent to the basic geometry of caged disc valves and degeneration of the disc occluder and strut fracture. Also hemolysis with disc prostheses is especially common.

An example a tilting disc valve is found in U.S. Pat. No. 4,892,540. Tilting disc valve prostheses have proved to be more satisfactory than the caged disc valves. The tilting disc valve prostheses generally have less hemolysis, lower cross valve gradients, and little wear of carbon pyrolyte discs. However, the tilting disc prostheses have a tendency to clot, and a strict anticoagulant regimen is required. Also movement of the disc in close relation with the sewing ring generally increases chances of interference by contact with adjacent mural endocardium or aortic intima and requires extra care be taken to prevent interference with movement of the disc.

A second replacement type of heart valve prothesis is the "tissue-type" valve which structurally resembles and functions similarly to at least one of the human heart valves. Such valves are most often harvested from pigs or cows and are mounted on a prosthetic stent with an affiliated sewing ring for attachment to the annulus of the valve being replaced. Problems related to the requirement for anticoagulants are usually short term with "tissue-type" valves and failure of such valves is seldom abrupt.

However, such valves are generally slowly rejected from the patient as a foreign body. The rejection is manifested as motion limiting calcification of the leaflets of the "tissue-type" valve and slowly ensuing functional failure. Such failure commonly necessitates replacement within fifteen years of original implantation. Examples of devices which apply to human and other animal "tissue-type" valvular prostheses are found in U.S. Pat. Nos. 3,656,185 and 4,106,129. Two examples of currently manufactured and marketed "tissue-type" valves are the MITROFLOW™ Heart Valve by Mitroflow International, Inc., 11220 Voyager Way, Unit 1, Richmond, B.C., Canada V6X 351 and Bovine Pericardial Valve by Sorin Biomedical, S.P.A., 13040 Saluggia (VC), Italy.

BRIEF SUMMARY AND OBJECTIONS OF THE INVENTION

In brief summary, is novel invention alleviates all of the known problems related to the substantial and long term requirement for administrating anticoagulants, "tissue-type" rejection, stenotic operation especially with a low profile valve prostheses, thrombogenesis, and post placement infection. The invention is a long-lasting implantable prosthetic heart valve which contains no tissue component.

The valve leaflet apparatus is produced as a unicast or extruded prosthetic valve leaflet apparatus and is devoid of tilting or traveling metal or plastic components. The invention comprises a stent which provides an implanting support for the valve leaflet apparatus. The stent has a novel sewing ring which provides a hard surface component to which anchoring sutures are tied and an optionally used soft component against which the anchoring valve receiving orifice of the heart is free to compliantly expand and contract as the heart beats.

The stent comprises a frame which is fully covered by a biochemically inert or physiologically compatible shroud. The frame is generally a light weight, hollow cylinder, machined or trimmed to provide a suturing support ring, extended cusp stanchions, and interference free blood flow to the coronary arteries. The frame is joint free and is slightly deformable to conform to contractile changes of the heart.

The shroud comprises two or three parts, depending upon use of the valve. A first part of the shroud comprises a hollow cylindrical seamless material which has substantially the same diameter as the frame. The seamless material is inserted into the cylinder of the frame and folded outward and downward at the top and outward and upward at the bottom such that the top and bottom parts meet at a site at the mere medial part of the suturing support ring. If the :shroud is made of two parts, each top and bottom part is folded outward at the site to form a contiguous two-layered brim. The brim provides the hard surface component forming a sewing ring for suturing the stent for the anchoring sutures. If the shroud comprises three parts, the top and bottom parts are folded outward to form two separated sewing rings.

Above the sewing ring or rings, the shroud is trimmed and sewn or otherwise fused together such as by heat bonding to conform to the shape of the frame and provide an encompassing cover therefor. When the sewing rings are separated, a soft, compliant material is interposed to provide a cushion between the stent and the natural orifice in which the valve resides between the two sewing rings.

Another part of each shroud is a brim cover. In the case of the two part shroud, the brim cover comprises a cylinder of material surrounding, folded over, and securely sutured to the two-layered brim to provide a tissue adhering cover above and below the brim. For the three part shroud, the brim area also comprises a cylinder of material. However, in this latter case, more central portions of the brim cover are folded and inserted between The interfaces between each brim and the soft compliant material, thereby providing a continuous tissue adhering cover which covers each brim, the soft compliant material and interface there between. Each brim cover is selectively complexed and impregnated with antibiotics to reduce the likelihood of infections, anticoagulant and endothelial cells or endothelial growth factors to selectively control incorporation of surrounding tissue of the natural orifice interface.

The valve leaflet apparatus comprises a multiple leaf valve which resembles in form and function a natural heart valve. The valve is a resilient synthetic resinous material part having an outside diameter which is substantially the same size as the stent. The valve leaflet apparatus may be formed by molding or extruding. The valve comprises a plurality of cusps which form medially disposed leaves which coapt upon closure to reduce leaflet wear and tear. When the synthetic resinous material from which the valve is molded is porous and chemically compatible, it is selectively complexed and impregnated with antibiotic medications to decrease the risk of post placement valve infection and anticoagulants to totally eliminate the need for initial exogenous anticoagulation on the part of the patient. The valves are sutured or otherwise permanently attached to the stent.

Accordingly, it is a primary object to provide a prosthetic heart valve having a mean-time-to-failure which is substantially longer than the expected life span of the patient.

It is another primary object to provide such a durable prosthetic heart valve which is simple in construction and low in manufacturing cost.

It is a significant object to provide a prosthetic heart valve configured entirely of biochemically-inert and biocompatible materials.

It is another significant object to provide a heart valve which is devoid of adhesives or bonding resins which might be released into the bloodstream of a receiving patient over a period of time.

It is another significant object to provide a prosthetic heart valve comprising an artificial leaflet valve mechanism which is similar to a natural valve in shape and function and which is assembled into a stent which provides mounting support for the valve in a native orifice from which a natural valve has been excised.

It is another significant object to provide the prosthetic heart valve with a sewing ring comprising a superior and an inferior hard surface against which knots in anchoring sutures are securely affixed.

It is a key object to provide at least one embodiment of a prosthetic heart valve configured to replace a natural mitral valve.

It is another key object to provide at least one embodiment of a prosthetic heart valve conformably configured to replace a natural aortic valve.

It is another key object provide the prosthetic heart valve with a soft potion interposed between superior and inferior hard valve anchoring surfaces which perimetrically expands between the the hard surfaces and a juxtaposed natural and somewhat irregular native valve annulus to form a conformable seal.

It is still another key object to provide the soft portion comprising material which comprises a cover, the surface of which is permissive only to limited tissue ingrowth such that the soft portion is separable from the native valve annulus should removal of the valve become necessary.

It is fundamental object to provide a stent which comprises a frame, a frame shroud or cover comprising a two part sewing ring which encompasses at least a large measure of the frame, and optional additional cover parts which cover otherwise uncovered parts of the frame in the area where the sewing ring is attached to the native valve orifice.

It is significant object to provide a stent which permits the prosthetic valve to deform slightly with heart motion thereby permitting leaflets of the valve mechanism to coapt with a sliding motion to reduce wear at the free margins of the leaflets.

It is another significant object to provide a stent frame which is capable of annular deformity and slight perimetric expansion such that the stent frame diametrally varies expansively and contractually with the natural valve orifice within which the stent frame is disposed, It is another significant object to provide a stent which permits the prosthetic valve to expand and contract with the natural valve orifice in which the prosthetic valve resides to reduce tugging forces upon the sutures and thereby reduce the likelihood of eventual valve dehiscence.

It is a basic object to provide a stent frame comprised of metal or synthetic resinous material which describes a continuous, seamless circular plane.

It is an essential object to provide a stent frame which comprises a plurality of circumferentially-spaced, axially projecting cusp supports.

It is consequential object to provide a stent frame comprising a plurality of windows which reduce the weight of the stent frame.

It is another object to provide a stent frame comprising a series of holes therein which allow margins of a valve leaflet apparatus to be securely affixed to the stent frame.

It is vital object to provide a double walled shroud of bio-compatible material which covers at least a large measure of the stent frame.

It is another vital object to provide the double walled envelope which comprises pockets which receive and cover the cusp supports of the stent frame.

It is another significant object to provide a stent frame enveloping cover which comprises superior and inferior members of a sewing ring by which the prosthetic heart valve is sewingly affixed about the native valve orifice.

It is another fundamental object to provide the double walled stent frame enveloping cover comprising a continuous connection to each sewing ring.

It is another important object to provide at least one sewing ring comprising a firm, knot supporting inferior and superior surface for sewingly affixing the prosthetic heart valve to the native valve orifice.

It is another key object to provide a cover for the sewing rings and a soft, deformable, space filling material intermediate portion interposed between two sewing rings, the space filling material perimetrically expanding to fill and seal against a native valve annulus when the sewing rings are drawn tightly into place around the annulus.

It is another key object to provide a soft, deformable intermediate portion which comprises material which results in variable incorporation of surrounding tissue, thereby providing optimal balance between ease of removal and prevention of infection.

It is a notable object to provide a cover for the stent frame at least a part of which is impregnated with at least one active biochemical from a group comprising antibiotics, anticoagulant medications, endothelial cells or endothelial cell growth factors.

It is a main object to provide a heart valve leaflet apparatus which resembles in form and function a human trileaflet heart valve.

It is another main object to provide a valve mechanism which comprises no centrally disposed members during the time the valve is open.

It is another main object to provide a valve leaflet apparatus comprising members which move toward the inner surface of the stent when the valve is coursed with maximum flow thereby providing a valve having a flow cross section substantially as large as the stent.

It is another notable object to provide a valve mechanism which comprises a trileaflet configuration of substantially the same dimensions as a natural aortic valve thereby providing a prosthetic valve of relatively low silhouette compared to a caged ball valve.

It is another fundamental object to provide a valve mechanism which comprises a functionally continuous surface over all aspects of the valve.

It is a principal object to provide a valve mechanism which is non-thrombogenic.

It is another notable object to provide at least one valve leaflet apparatus which is impregnated with anticoagulant medication to eliminate the need for initial exogenous anticoagulation on the part of the patient.

These and other objects and features of the present invention will be apparent from the detailed description taken with reference to accompanying drawings.

BRIEF DESCRIPTION OF THE DRAWINGS

FIG. 4 is a perspective of steps following the step of FIG. 3 in the stent assembly process wherein the covering material is folded outward and over the frame at both the top and bottom and then folded outward to form double brim sewing rings of the implantable prosthetic aortic heart valve.

FIG. 5 is a perspective of a partially completed aortic heart valve stent with the covering trimmed along dashed lines seen in FIG. 4 to encompass rising cusp supports of the frame.

FIG. 10 is a perspective of a heart valve leaflet apparatus.

FIG. 11 is a section along lines 11—11 of FIG. 10.

FIG. 12 is a top elevation of a closed trileaflet valve.

FIG. 13 is a top elevation of an open trileaflet valve.

DETAILED DESCRIPTION OF THE ILLUSTRATED EMBODIMENTS

Reference is now made to The embodiments illustrated in FIGS. 1–22 wherein like numerals are used to designate like parts throughout.

Figure 1:
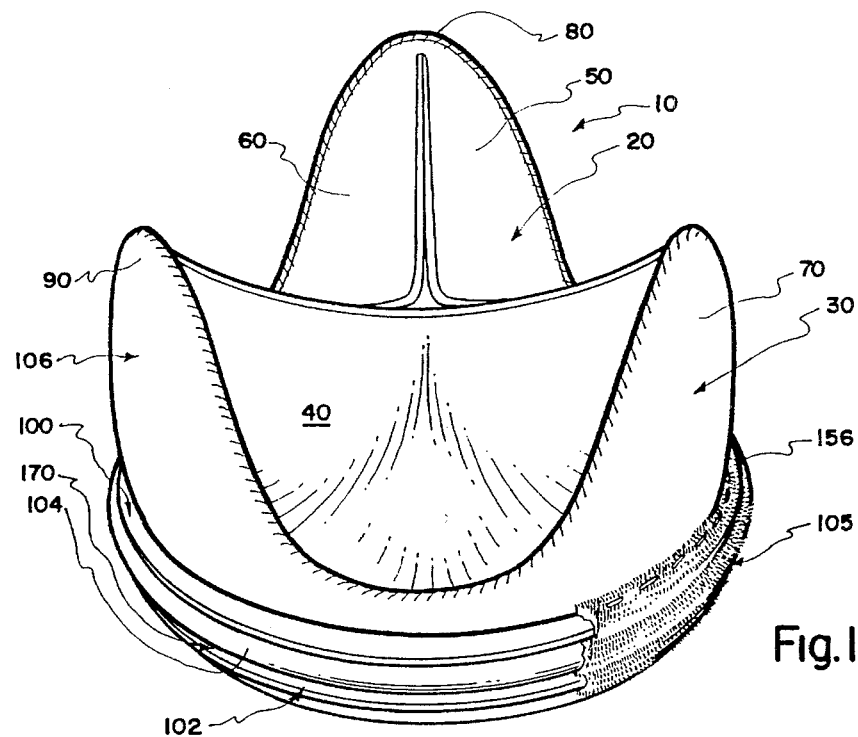
FIG. 1 is a perspective of an implantable prosthetic aortic heart valve comprising a heart valve leaflet apparatus suitably joined to a supporting stent and brim-formed double sewing rings seen partially covered by a brim cover, a portion of the brim covering portion of the apparatus being removed to reveal other details of the sewing rings.

A first illustrated embodiment of the invention, seen in FIG. 1, is a prosthetic aortic heart valve 10. Aortic heart valve 10 comprises a heart valve leaflet apparatus 20 and a heart valve leaflet apparatus supporting stent 30. Heart valve leaflet apparatus 20 is disposed medially to stent 30 and therein comprises three cusps 40, 50, and 60 which are similar in form and function to cusps of a natural heart valve. Stent 30 comprises three upright, cusp supports 70, 80, and 90, each of which provides a vertical stay for the cusps 40, 50, and 60.

Further, in this embodiment, aortic valve 10 comprises two radially projecting sewing rings 100 and 102. Interposed between sewing rings 100 and 102 is a soft, deformable intermediate natural valve orifice interfacing portion 104, the purpose and character of which is provided in detail hereafter.

Seen in part, covering sewing rings 100 and 102 and interfacing portion 104, is a brim cover 105. Brim cover 105 is described in detail hereafter.

Figures 2, 3:
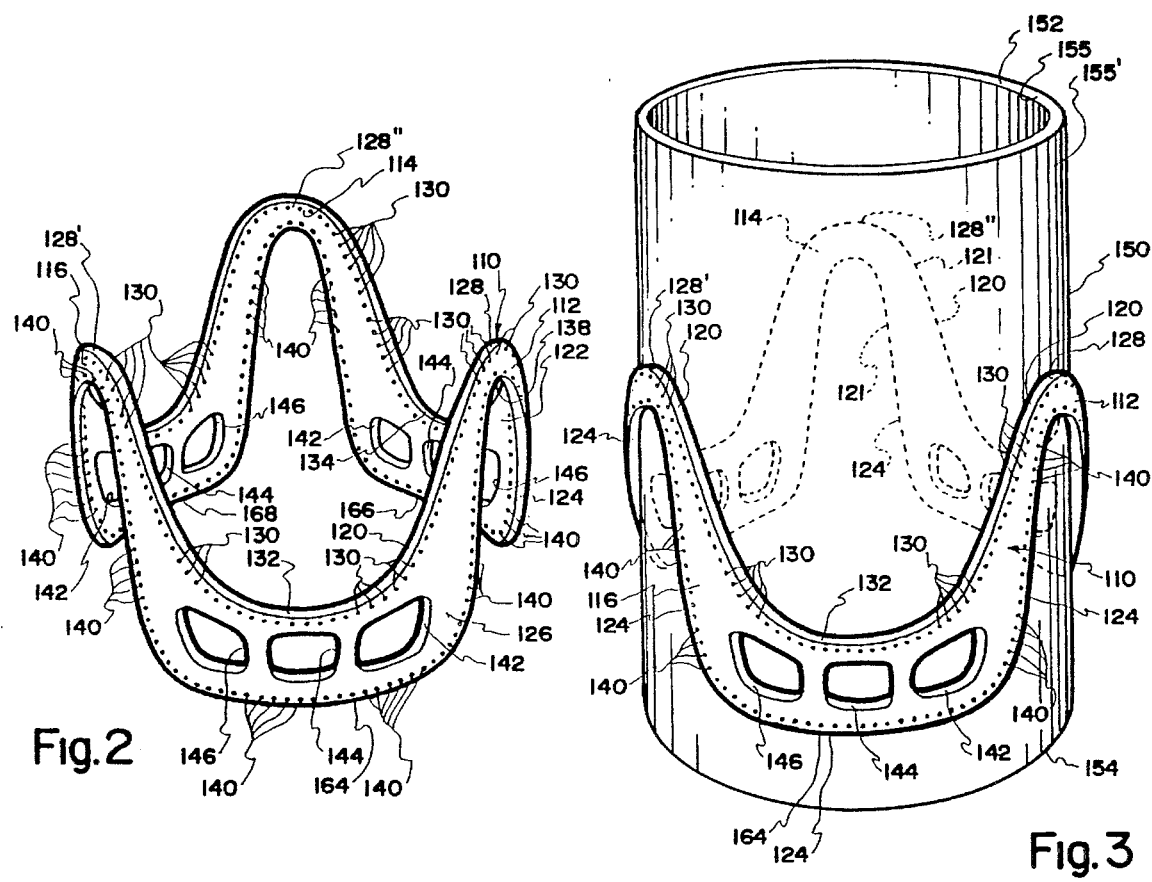
FIG. 2 is a perspective of the frame of the stent.
FIG. 3 is a perspective of the frame and a length of foldable cylindrical covering material disposed therein as a first step in a stent assembly process.

While sewing rings may be differently constructed within the scope of the invention, in this first illustrated embodiment, sewing rings 100 and 102 are contiguous segments of a stent cover 106 which, in large measure, covers and protects a supporting frame 110, seen in FIG. 2, from biologic activity. The reasons for so making and the method for fabricating sewing rings 100 and 102 is covered fully below.

Frame 110 is generally of a continuous hollow cylindrical form and is substantially rectangular in cross section. Although frame 110 is completely covered and sealed from biological fluids in each implanted aortic valve 10, the material selected for frame 110 is non-corrosive, fatigue resistant, and substantially biologically inert. As such, frame 110 may be made from stainless steel or a carbon based material such as pyrolytic carbon on a graphite substrate. However, frame 110 may be made from materials having comparable weight, biocompatibility, flexibility, and strength characteristics similar to the materials of preference within the scope of this invention.

To provide support for stent 30 and the three superior circumferential edges of cusps 40, 50, and 60 of valve leaflet apparatus 20, frame 110 comprises three inverted "U" shaped stanchions 112, 114, and 116. In this first illustrated embodiment, each of the stanchions 112, 114, and 116 are identical. For this reason, only stanchion 112 will be described in detail with the understanding the description of stanchion 112 applies equally to stanchions 114 and 116.

Inverted "U" shaped stanchion 112 comprises a superior edge 20, an inner surface 122, an inferior edge 124, and an outer surface 126, as best seen in FIG. 2. At the highest point, inverted "U" shaped stanchion 112 comprises an apex 128 superiorly disposed on edge 120. Similarly, stanchion 114 comprises an apex 128" and stanchion 116 comprises a stanchion 128'. Disposed below apex 128 and inferior to superior edge 120, frame 110 comprises a plurality of holes, generally numbered 130, disposed between surfaces 122 and 124. Holes 130 are provided for the purpose of sewing corresponding margins of the heart valve leaflet apparatus 20 to stent 30. For this reason, superior edge 120 is arcuately formed to follow a path which provides a margin superior to holes. Thus, edge 120 arcuately follows a distally descending path from apex 128 to a most inferiorly disposed medial point 132 where stanchion 112 extends to circumferentially smoothly connect to stanchion 116. Edge 120 similarly descends distally from apex 128 on the other side of stanchion 112 to an inferiorly disposed medial point 134 extending circumferentially to connect smoothly to stanchion 114.

Inferior edge 124 comprises an apex 138 disposed immediately below apex 128 and offset from apex 128 to provide inferiorly disposed support for attaching marginally disposed portions of heart valve leaflet apparatus 20 associated with cusps 40 and 50, as is described in detail hereafter. As seen in FIG. 2, proximally disposed in a margin of frame 110 above inferior edge 124, are a plurality of holes, generally numbered 140, disposed between surfaces 122 and 126. Holes 140 comprise a second set of holes inferior to holes 130 through which heart valve leaflet apparatus 20 is also sewingly or otherwise attached to stent 30. While attachment of the heart valve leaflet apparatus 20 to stent 30 is described to be accomplished by sewing, one who is skilled in the art would understand that other methods of attachment, such as by a plastic connector or by fusing parts together through the holes, generally numbered 130 and 140, are within the scope of the invention.

As seen in FIG. 2, superior edge 120 and inferior edge 124 combine to describe the inverted "U" shape of stanchion 112. Flexibility of the material used to make frame 110 in combination with the inferior opening of the inverted "U" of stanchion 112 provides a frame capable of annular deformity and slight perimetric expansion. Such deformity and expansion permits the frame to compliantly respond to expansion and contraction of the native valve orifice of the beating heart in which aortic valve 10 is implanted to reduce beat by beat stress on aortic valve 10 anchoring sutures and thereby reduce the likelihood of eventual valve dehiscence. Also, to reduce the likelihood of valve dehiscence, the mass of frame 110 is reduced by excising material which is essentially unnecessary for strength, but which adds to the weight of frame 110 and therefore of stent 30. Therefor, windows 142, 144, and 146 are formed as best seen in FIG. 2.

Reference is now made to FIGS. 3–5 wherein the steps used to cover at least a large measure of frame 110 are seen. As seen in FIG. 3, the covering is a cylindrical seamless section 150 of material which is essentially biologically inert. A material such as GORTEX™, a polytetrafluoroethylene (PTFE) composite is preferable, however materials such as continuous knit a commercially available, medical grade DACRON™ velour such as a knitted velour polyester (polyethylene glycol terephthalate) or other materials having biochemically inert and compatible characteristics similar to those of PTFE derivatives may be used. All GORTEX™ materials referenced hereafter are products of and available from W. L. Gore and Associates, Inc., Medical Products Division, P.O. Box 900, Flagstaff, Ariz. 86002. Section 150 is of substantially the same exterior diametrical size as the interior diameter of frame and comprises a length which exceeds twice the height of stanchions 112, 114, and 116 for reasons which are described in detail hereafter. Section 150 comprises a top edge 152, a bottom edge 154, an inside surface 155, and an outside surface 155'.

As a first step in covering frame 110, section 150 is inserted into frame 110 as seen in FIG. 3 to cover inner surface 122. That portion of frame 100 which is hidden from view by the insertion of section 150 is shown by dashed lines 121.

As seen in FIG. 4, the top edge 152 of section 150 is folded radially outward and downward until the originally outside disposed surface 155' of section 150 rests upon apex 128 of stanchion 112 and resides similarly upon apex of stanchion 16 and upon apex 128" of stanchion 114 whereby the originally inside disposed surface 155 forms an outside sidewall 156. So downwardly extended, section 150 comprises sufficient length such that edge 152 is everted radially outward to form a brim 158.

Thus brim 158 is a continuous, seamless extension of sidewall 156, along a connecting line 156'. The originally inside disposed surface 155 of section 150 therefore becomes a superior surface 160 and the originally outside disposed surface 155' of section 150 becomes an inferior surface 162 of brim 158. Brim 158 extends radially outward a sufficient distance from the vertical portion of sidewall 156 to provide a superiorly disposed sewing ring 100. Sewing ring 100 comprises a width which is adequate for aortic valve 10 implanting purposes as is well known in the art.

Similarly bottom edge 154 is turned outward and upward until originally outside disposed surface 155' is in firm contact with an inferior segment 164 of inferior edge 124 of frame 110 between stanchions 112 and 116 (see also FIGS. 2 and 3). Inferior segment 164 is seen as a hidden dashed line in FIG. 4. Thereat, originally outside disposed surface 155' is likewise in firm contact with each inferior segment 166 and 168 (see FIG. 2) which resides between stanchions 112 and 114 and stanchions 114 and 116, respectively. So disposed, inferior edge 154 is everted outward to form a second brim 170. Thereby originally inside disposed surface 155 forms an exterior inferior sidewall 172 which forms a contiguous, seamless connecting line with an inferior side 174 of brim 170. Similarly, originally outside disposed surface 155' forms a contiguous, seamless connection 174' with a superior side 176 of brim 170. In aortic heart valve 10, the width of brim 170 is similar to the width of brim 158 thereby providing a second sewing ring 102 of substantially the same dimensions as sewing ring 100 but separated therefrom as seen in FIG. 4.

Figure 6:
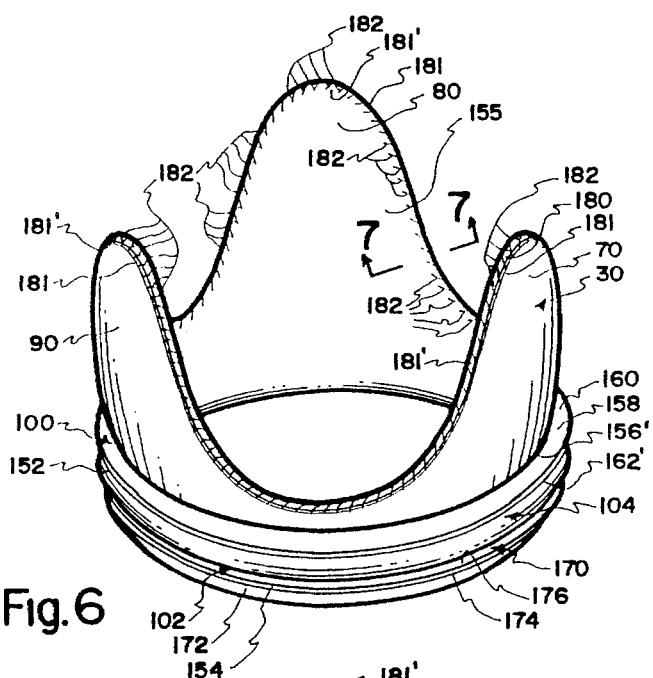
FIG. 6 is a perspective of a covered aortic heart valve stent wherein the trimmed cover is sewn together.

Following the pattern of the superior edge 120 seen as dashed lines 121 in FIG. 4, material is trimmed away along trim line 180 along a pattern superior to edge 120 to reveal parted edges 181 and 181' as seen in FIG. 5. Sufficient material is retained superior to edge 120 to close and completely cover superior edge 120 of frame 110 by tightly sewing parted edges and 181' together along trim line 180, as seen in FIG. 6.

Sewing to join parted edges 181 and 181' together is currently preferred; however, the parted edges 181 and 181' may be tightly bonded together by other methods such as heat fusing. The method of bonding depends upon the frame covering material selected. In any event, the edges are tightly bound together and completely cover frame 110 along edge 120, as seen in FIG. 6. So covered, stent 30 comprises the three cusp supports 70, 80 and 90 respectively supported by covered stanchions 112, 114, and 116.

Reference is now made to FIGS. 6, 7 and 16–19, wherein additional details of construction of stent 30 are seen. Stent 30 is particularly configured for use as an aortic valve. As a natural aortic valve orifice, in which aortic valve 10 is implanted, comprises tissue which changes the lateral dimensions of the natural valve orifice during each cycle of a beating heart, it is important to compensate for those changes to reduce effects which might increase the likelihood of valve dehiscence due to structural failure of the sewing ring, sutures, or natural tissue surrounding the valve.

For these reasons, stent comprises the flexible frame 110, as earlier described, which responsively reacts to expansion and contraction of the natural valve orifice. Also, an intermediate, orifice size compensating and interfacing portion 104 is disposed between sewing ring 100 and 102 and to provide a soft elastically compressible space filling component which perimetrically expands and compresses to effect a good annular seal between frame 110 and the natural orifice by valve 30. As seen in FIG. 6, the orifice interfacing portion 104 is externally and peripherally disposed about frame 110 between superiorly disposed sewing ring 100 and inferiorly disposed sewing ring 102.

Natural valve interfacing portion 104 is preferably formed to be a contiguous ring of material which is compressible, but which comprises memory which responsively expands to fill space previously vacated and unfilled by the remainder of stent 30 when compressive pressures are relieved. Such material may be non-expanded GORTEX™. However, interfacing portion 104 may be a linear segment of deformable material sewn or otherwise secured end-to-end to form a continuous ring.

When the interfacing and sewing ring materials are biochemically inert such that tissue does not adhesively attach thereto, brim cover 105 is used to provide the interface between the natural excised valve orifice and implanted prosthetic heart valve. Referring again to FIG. 1, a portion of brim cover 105 is seen on the right viewing side of aortic heart valve 10. As seem therein, brim cover 105 covers each sewing ring 100 and 102 and the orifice interfacing potion 104 disposed therebetween.

Brim cover 105 is preferably made from a material which is permissive to tissue in-growth so that a degree of adhesion improves adhesion of the grafted valve within the native excised valve orifice. Such material is preferably velour dacron a commercially available, medical grade DACRON™ but other relatively biologically compatible, biologically inert and physiologically stable materials may be used within the scope of the invention. A detailed description of the process for making and attaching brim 105 is provided hereafter. One important factor in the selection of materials for brim cover 105 is the choice of materials which may be complexed with appropriate biochemicals from a group comprising antibiotics, anticoagulant medications, endothelial cells or endothelial cell growth factors.

Incorporation of complexed antibiotics about the site of the excision significantly reduces the risk of post placement infection thereat, potentially reducing the amount of otherwise administered antibiotics and relieving the valve 10 recipient of a post placement antibiotics regimen. Incorporating complexed anticoagulants when possible, in prosthetic leaflet apparatus 20, reduces or eliminates the need for an initial exogenous anticoagulation regimen on the part of the valve recipient. Such a regimen is currently common place for prosthetic heart valve recipients.

Figure 7:
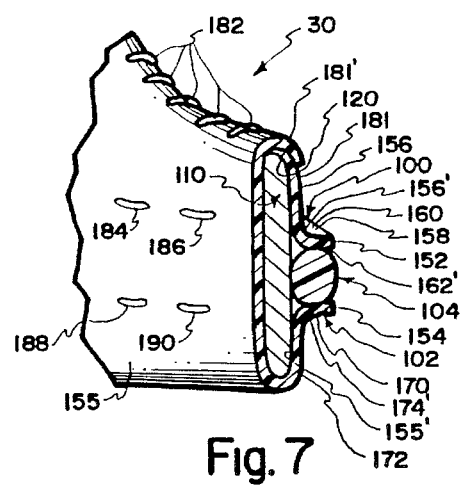
FIG. 7 is a section along lines 7—7 of FIG. 6.

A cross section of stent 30 made along line 7—7 in FIG. 6 is seen in FIG. 7. The cross section of stent 30 comprises frame 110 totally enclosed by material of section 150 and interfacing portion 104. As seen the rein, material remaining after being parted along trim line 180 is folded to form a seam along superior edge 120 of frame 110 and tightly bound thereat with a plurality of sutures 182 to close parted edge 181' over parted edge 181.

Additional sutures, represented by sutures 184 and 186 in FIG. 7, tightly bind sewing ring 100 through windows and inferiorly disposed openings in frame 110 to outside sidewall 156 along seamless connection line 156'. Similarly, sewing ring 102 is tightly bound through the windows and inferiorly disposed openings in frame 110 to exterior inferior sidewall 172 along seamless connection line 174' by sutures, represented by sutures 188 and 190 in FIG. 7. All such sutures used in valve 10 and similarly constructed valves preferably constitute GORTEX™ 3-0 suture material. However, other strong, long-lasting suture material which is essentially biochemically inert and of other preferable sizes can be used within the scope of the invention.

The ring comprising interfacing portion 104 is snugly inserted between sewing rings 100 and 102 and firmly affixed thereat by additional sutures or by a ring-tight fit against frame 110 between sewing rings 100 and 102. Thus covered, frame 110 is enclosed and substantially free from interfacing liquids and tissue which surround an operative valve 10.

Figure 14:
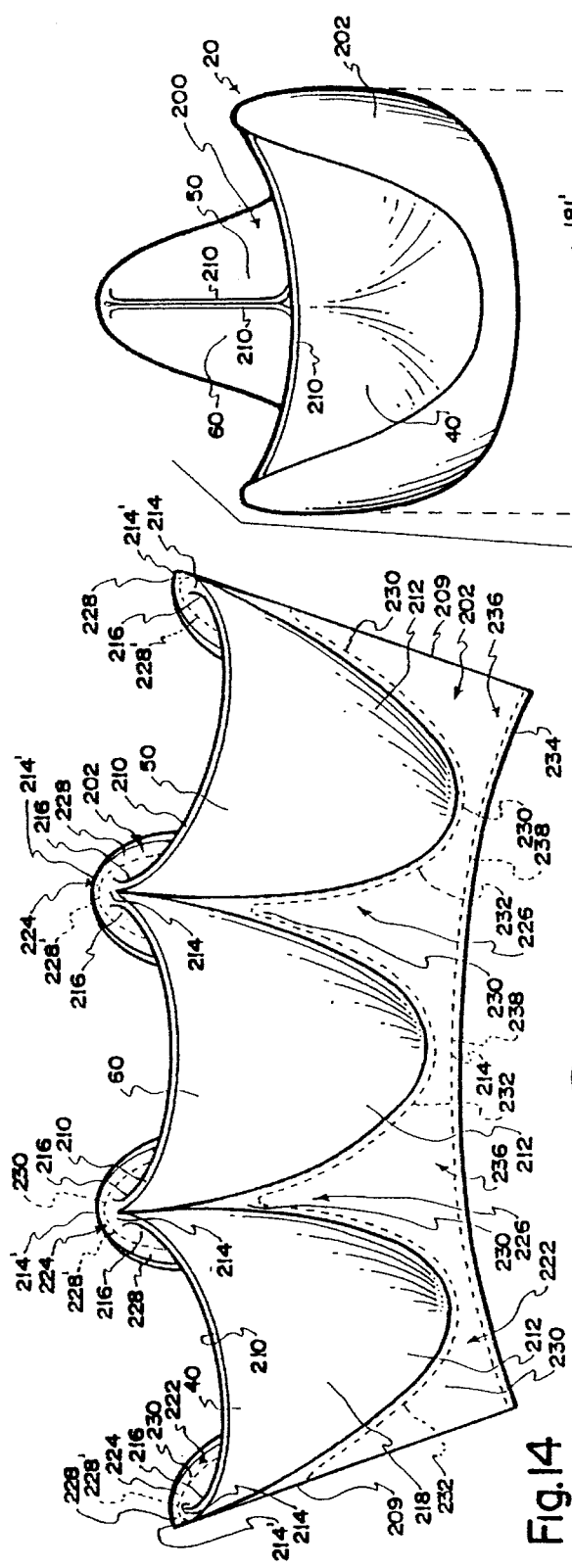
FIG. 14 is a perspective of the heart valve leaflet apparatus incised along line 14—14 in FIG. 10 and opened for clarity of presentation.
Figure 16:
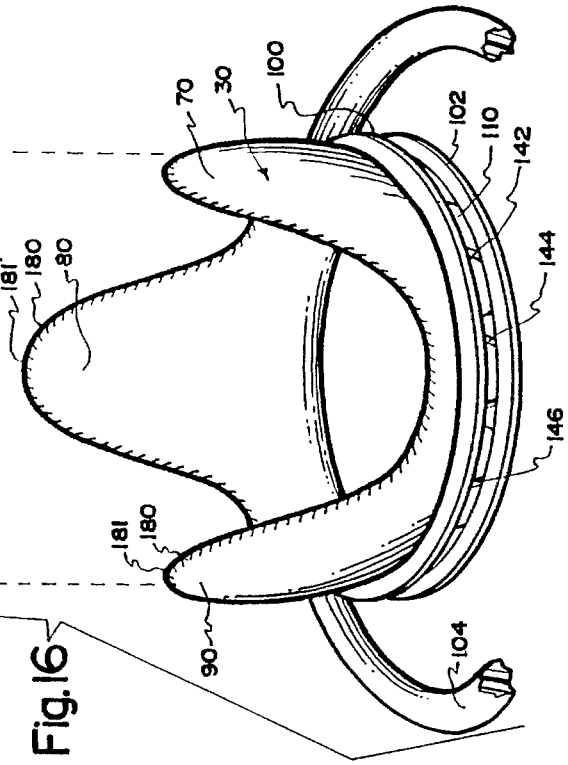
FIG. 16 is an exploded perspective of the heart valve prosthesis seen in FIG. 1.

In this first illustrated embodiment, heart valve leaflet apparatus 20 comprises it prosthetic trileaflet valve apparatus 200 which is operatively similar to a natural aortic heart valve. See FIG. 10. Heart valve leaflet apparatus 20 comprises a support collar 202 and thereto integrally connected leaflet cusps 40, 50, and 60 of prosthetic trileaflet valve apparatus 200. In FIG. 14, heart valve Leaflet apparatus 20 is excised along line 209, seen in FIG. 10, and opened to provide a view of the inside of cusps 40, 50, and 60 and collar 202. FIG. 11 comprises a section along lines 11–11 of FIG. 10 and shows the unitary construction of heart valve leaflet apparatus 20 and attachment between collar 202 and cusps 40 and 50 of prosthetic apparatus 200.

In a natural aortic heart valve, the cusps are individually identifiable as an anterior cusp, a left posterior cusp, and a right posterior cusp. Identifying features of the anterior cusp and left posterior cusp are depressions for connecting coronary arteries. In prosthetic apparatus 200, each leaflet cusp 40, 50, and 60 is substantially like the others. For this reason, only one cusp 40 will be described in detail with the understanding that a like description applies for cusps 50 and 60 as well.

Cusp 40 comprises a thickened superior edge which forms a commissure or lip 210 and a thin substantially uniform leaf membrane 212. In this embodiment, Cusp 40 is preferably molded as a unitary part of heart valve leaflet apparatus 20 and thereby comprises a thickened connecting intersection 214 disposed along the interface between collar 202 and commissure 210 and leaf membrane 212, as best seen in FIG. 11. The thickening of commissure 210 and connecting intersection 214 is necessary provide reliable structure where flexing and wear is the greatest in heart valve leaflet apparatus 20. As seen in FIG. 10, cusp 40 comprises an exterior facing side 216. An interior facing side 218 of cusp 40 is best seen in FIG. 14.

Collar 202 is a stent interconnecting structure which supports cusps 40, 50, and 60, substitutes for natural supporting structure in the native orifice and, thereby, provides an interface to stent 30. As such collar 202 rises to an apex 214' above connecting intersection 214 where collar 202 interconnects to each commissure 210. To provide effluent access for blood flow to the coronary arteries during diastole, collar 202 is dramatically decreased in vertical height between each apex 214' to a medially disposed Low point 214".

The connecting features of collar 202 are seen from an exterior perspective in FIG. 10 and from an interior perspective in FIG. 14. Collar 202 comprises an exterior side 220 and an interior side 222. The interface with each cusp 40, 50 and 60 is entirely disposed on interior side 222 of collar 202. Generally, inner side 222 is divided into a section 224 superior to the interface with each cusp 40, 50, and 60 and a section 226 inferior to the interface with each cusp 40, 50, and 60.

For the purpose of affixing each cusp 40, 50, and 60 solidly to stent 30 and, in particular, to frame 110 collar 202 comprises a superior binding margin 228 and an inferior binding margin 230. Superior binding margin 228 is disposed within superior section 224 and comprises an area adequate to suture collar 202 to stent 30 thereat. A dashed line 228' traces a portion of the suture trail within superior binding margin 228 in FIG. 14.

Similarly, inferior binding margin 230 is disposed within inferior section 226 and comprises an area adequate to suture collar 202 to stent 30 thereat also. Another dashed line 232 traces the suture trail inferiorly disposed to cusps 40, 50, and 60 in FIG. 14. As seen therein, collar 202 comprises a bottom edge 234 and a binding margin 236 immediately superior to bottom edge 234. A third suturing trail, seen as dashed line 238, is disposed within binding margin 236 for the purpose of providing a region for binding the bottom of collar 202 to stent 30 to eliminate any cavities of low or no liquid flow between collar 202 and stent 30.

While it is within the scope of the invention to provide prosthetic trileaflet valve apparatus having cusps which are manufactured separately and later affixed to a collar, it is preferred in this embodiment that heart valve leaflet apparatus 20 be cast as a unit or unicast. Methods for casting such a valve are well known in the art. One material which may be used is silicone. An advantage derived from the use of silicone is the opportunity for complexing with other materials, such as antibiotics to decrease the risk of post placement valve infection and anticoagulant medication to eliminate the need for initial exogenous anticoagulation on the part of the patient.

Referring to the section along lines 11—11 of FIG. 10 as seen in FIG. 11, continuity between cusp 40 and collar 202 is seen at juncture 240 and similar continuity between cusp 50 and collar 202 is seen at juncture 242. Each cusp 40 and 50 is seen to comprise a separate commissure 210 and a pliant leaf membrane 212 there below. The separation of each juncture 240 and 242 is seen to occur medial to superior binding margin 228 such that binding sutures do not impair movement of any leaf membrane 212.

Leaflet apparatus 20, comprising prosthetic trileaflet valve apparatus 200 and collar 202, is inserted to snugly fit into stent 30. So disposed, collar 202 is firmly affixed to stent 30 by suturing along dashed lines 228', 232, and 238. Suturing along dashed lines 228' and 232 comprises passing suturing materials through holes 130 and 140 circumferentially disposed in frame 110, as earlier described.. Suturing along dashed line 238 may alternatively attach collar 202 to sites inferior to edge 164 of frame 110 in inside surface 155 or directly through frame 110 through a series of holes therein which are not shown.

Thereby, heart valve leaflet apparatus 20 is firmly affixed to stent 30 to complete prosthetic aortic valve 10 providing an aortic replacement valve which comprises a soft portion 104 with a tissue compatible brim cover 105 for interfacing with an irregular native annulus from which the natural valve has been excised and hard surfaced sewing rings 100 and 102, also covered by brim cover 105, externally disposed upon the stent 30. As the sutures which anchor valve 10 in the native orifice pass through sewing rings 100 and 102 and are firmly, tightly affixed thereto, the deformable intermediate interfacing portion 104 and brim cover 105 perimetrically compress and expand to fill and seal against the irregular native valve annulus.

Reference is now made to FIGS. 12 and 13 wherein valve 10 is seen closed and opened, respectively. As seen in FIG. 12, each commissure 210 is aligned with the other two juxtaposed commissures 210 to substantially close valve 10. However, as each commissure 210 is not perfectly flexible and pliant, a triangular orifice 244 is formed which, if not otherwise closed, provides a regurgitant pathway through orifice 244 and a resulting valvular insufficiency. However, the flexibility of frame 110 and therefore stent 30 and the pliability of each leaf membrane 212 permits membranes 212 to coapt and close valve 10 at contacting surfaces inferior to commissures 210, exemplarily seen as contact lines 246 within triangular orifice 244.

When valve 10 is open, triangular orifice 244 is enlarged, providing a medially free passageway through which blood courses. Each commissure 210 and associated leaf membrane 212 is forced radially outward to provide an orifice operatively similar to a natural aortic valve orifice opening.

Figure 15:
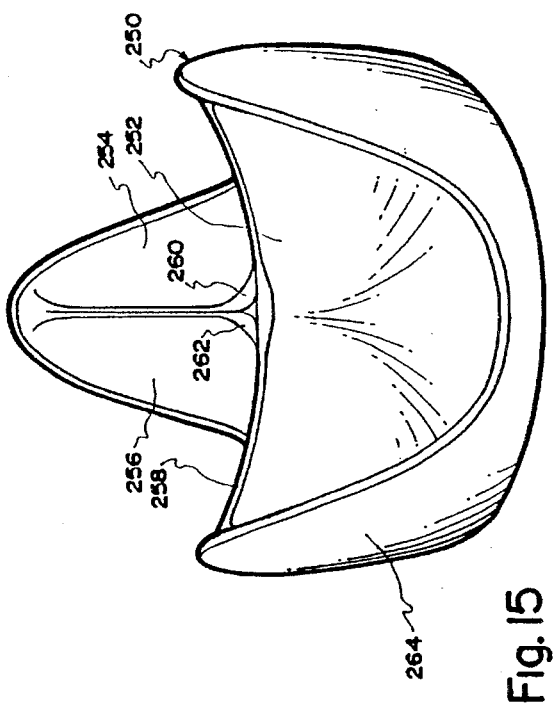
FIG. 15 is a perspective of a prosthetic heart valve leaflet apparatus wherein the leaflets are leaflet models cast from a mold of a natural heart valve.

A second illustrated embodiment of an aortic valve leaflet apparatus 250 is seen in FIG. 15. Aortic valve leaflet apparatus 250 is similar to heart valve leaflet apparatus 20 seen in FIG. 10, comprising three leaflets membranes 252, 254, and 256, each membrane 252, 254, and 256 comprising a superiorly disposed commissure 258, 260, and 262, respectively. However, in this case, the leaflet membranes 252, 254, and 256 are not alike. Similarly, each commissure 258, 260, and 262 is different from the other two commissures.

Such is the case because aortic valve leaflet apparatus 250 is produced from a mold of a natural valve. As such, the more medial portions of the each commissure 258, 260, and 262 comprises a thicker, non-uniform appearance associated with naturally grown valves. Material from which aortic valve leaflet apparatus 250 is made is the same as that specified for heart valve leaflet apparatus 20. The characteristics of a surrounding, mounting collar 264 are the same as that described for collar 202, including all cusp-collar interfaces and suturing lines.

Figure 8:
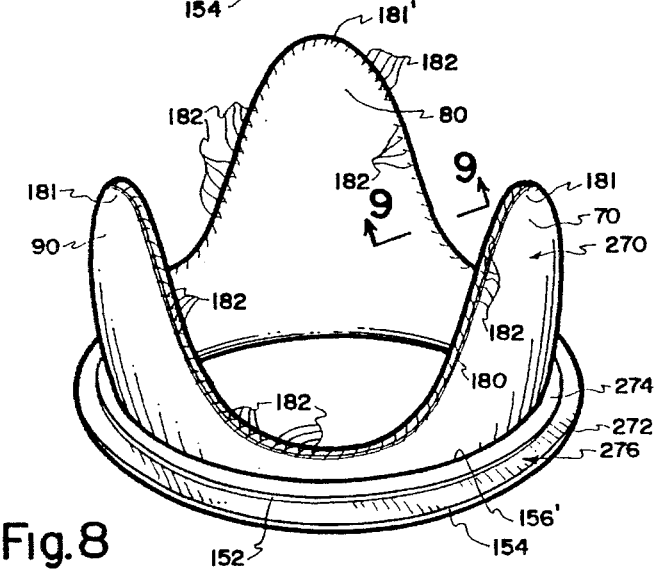
FIG. 8 is a perspective of a covered stent for a mitral heart valve prosthesis.
Figure 9:
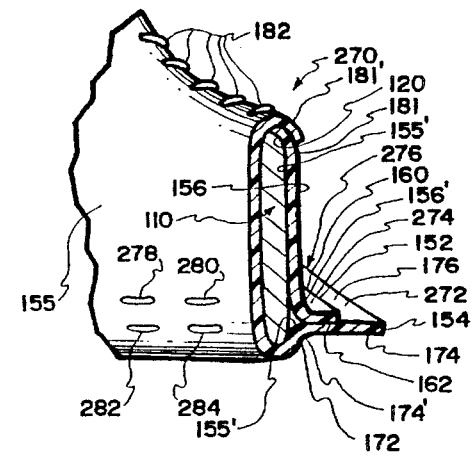
FIG. 9 is a section along lines 9—9 of FIG. 8.

Another illustrated embodiment for a stent 270 is seen in FIG. 8 and 9. Except for the steps of outward eversion of each brim, stent 270 is made as stent 30 is made. As is the case for stent 30, a section 150 of cylindrical material is used to cover frame 110. However, in this case, section 150 is disposed to entirely cover frame 110 and produce a stent preferably for a prosthetic valve used as a valve replacement in a native orifice having the geometry of an orifice similar to that from which a natural mitral valve has been excised. To provide a stent 270 with sewing rings which correspond to the funnel-like contour of an excised mitral valve orifice, the structure and steps in manufacture of the sewing ring forming brims are markedly different than similar steps in forming brims for stent 30.

Reference is again made to FIGS. 3–5 wherein the steps used to cover at least a large measure of frame 110 are seen. As seen in FIG. 3, the covering is cylindrical seamless section 150 of the same essentially biologically inert material used to make stent 30. The frame 110 covering process to the step of everting each edge 152 and 154 outwardly to form a brim is the same as the covering steps for stent 30.

Therefore, as the first step in covering frame 100 to make stent 270, section 150 is inserted into frame 110 as seen in FIG. 3 to cover inner surface 122. As seen in FIG. 4, the top edge 152 of section 150 is folded radially outward and downward until the outside surface 155' of section 150 rests upon apex 128 of stanchion 112 and resides similarly upon apex 128' of stanchion 116 and upon apex 128" of stanchion 114 whereby inside surface 155 forms an outside sidewall 156.

Similarly bottom edge 154 is turned outward and upward until outside surface 155' is in firm contact with an inferior segment 64 of inferior edge 124 of frame 110 between stanchions 112 and 16 and is likewise in firm contact with each inferior segment 66 and 168 which resides between stanchions 112 and 114 and stanchions 114 and 116, respectively. So disposed, inferior edge 154 is everted outward to form an inferiorly disposed wide brim 272. See FIG. 8. Thereby inner surface 155 forms an exterior inferior sidewall 172, see FIG. 9, which forms a contiguous, seamless connecting line 174' with an inferior side 174 of brim 272. Similarly, originally outside surface 155' forms a contiguous, seamless connection with a superior side 176 of brim 272.

The downwardly extended portion of section 150 comprises sufficient length such that edge 152 is everted radially outward to form a narrow brim 274 in direct contact with brim 272. The originally inside disposed surface 155 of section 150 therefore becomes a superior surface 160 and the originally outside surface 155' of section 150 becomes an inferior surface 162 of narrow brim 274. Thus brim 274 is a continuous, seamless extension of sidewall 156, along connecting line 156'.

Note that, in the case of stent 270, the eversion of edge 152 occurs at a site inferior to the eversion of brim 158 of stent 30. Brim 274 extends radially outward a sufficient distance from the vertical portion of sidewall 156 to provide a connecting surface with brim 272 to form a single sewing ring 276. As seen in FIG. 8, sewing ring 276 comprises a width which is adequate for excised mitral valve orifice implanting purposes as is well known in the art.

The steps of trimming material along trim line 180 and joining parted edges 181 and 181' together are the same as for scent 30.

FIG. 9 shows a cross section of scant 270 made along line 9—9 in FIG. 8. The cross section of stent 270 comprises frame 110 totally enclosed by material of section 150. As seen therein, material remaining after being parted along trim line 180 is folded to form a seam along superior edge 120 and tightly bound thereat with a plurality of sutures 182 to close parted edge 181' over parted edge 181.

Figure 19:
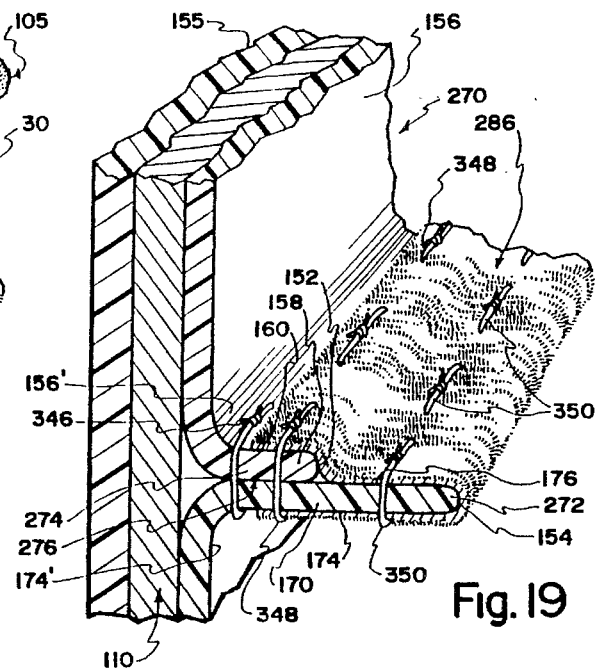
FIG. 19 is an exterior perspective of a medial section of the mitral heart valve prosthesis stent of FIG. 9 showing the cylinder of material seen in FIG. 17 disposed about and securely affixed to the brim of the mitral valve stent.

Additional sutures, represented by sutures 278 and 280 in FIG. 9, tightly bind brim 274 through windows and inferiorly disposed openings of frame 110 to inner surface 155 along seamless connection line 156'. Similarly, sewing ring 276 is tightly bound through the windows and inferiorly disposed openings in frame 110 to inner surface 155 along seamless connection line 174' by sutures, represented by sutures 282 and 284 in FIG. 9. All such sutures used in stent 270 are preferably GORTEX™ 3-0 suture material. However, other strong, long-lasting suture material which is essentially biochemically inert can be used within the scope of the invention. A brim cover 286, as seen in FIG. 19, for covering stent 270 sewing ring 276 is described in detail hereafter.

Thus covered, frame 100 is substantially free from interfacing liquids and tissue which surround an operative prosthetic mitral valve replacement.

Figure 21:
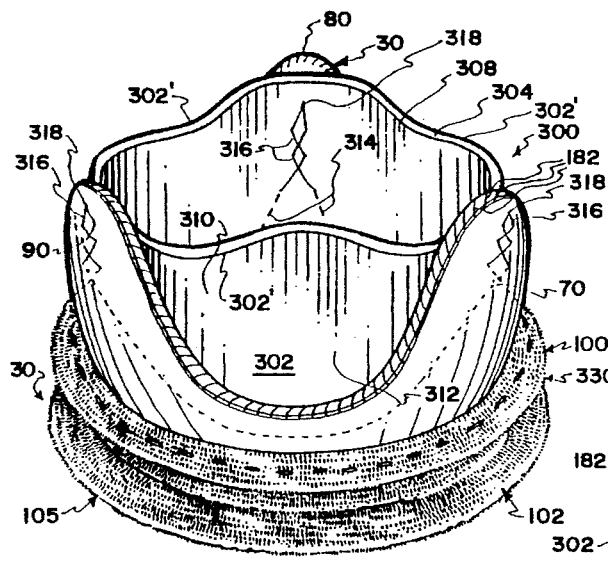
FIG. 21 is a perspective of the cylinder of material of FIG. 20 sewn into a stent to form an aortic valve prosthesis, said valve being seen in a nearly fully open configuration.
Figure 22:
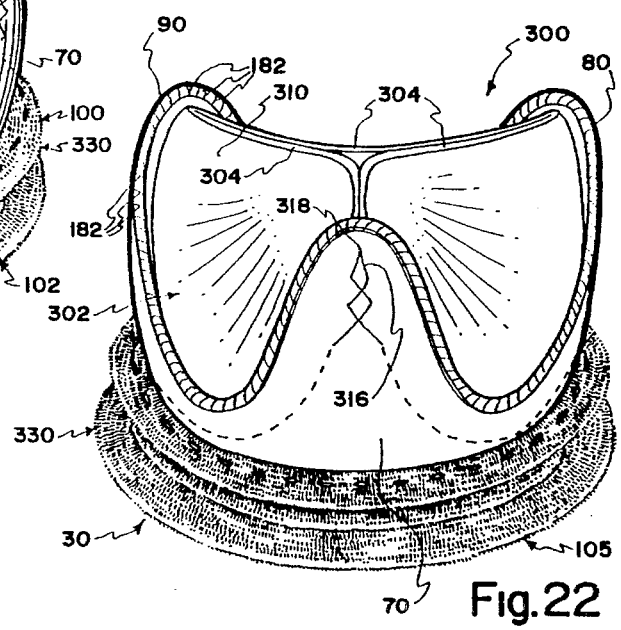
FIG. 22 is a perspective of the aortic valve seen in FIG. 21 rotated about a vertical axis and closed.

A third illustrated embodiment of a heart valve 300 is seen in FIGS. 21 and 22. Valve cusps are formed from a single piece of material, such as a hollow .cylinder of material 302 seen in FIG. 20. Cylinder 202 may be formed by a cylindrical extrusion or by suturing vertical edges together. Material cylinder 302 comprises a substantially planar superior edge 304 and an oppositely disposed inferior edge 306. Further material cylinder 302 comprises an inner surface 308 and an outer surface 310 disposed between edges 304 and 306 forming cylindrical wall 312. Cylindrical wall 312 is of uniform thickness and is preferably thin and pliable, yet strong and enduring under pressure and flexure.

One material from which heart valve leaflet apparatus 20 may be made is a synthetic, stretchable polytetrafluoroethylene (PTFE) material known as GORTEX SURGICAL MEMBRANE™. GORTEX SURGICAL MEMBRANE™ is essentially biochemically inert, hydrophobic and non-thrombogenic. It has been used in pleural, peritoneal and pericardial reconstruction where absolute prevention of tissue adhesion to it is desired.

The outside diameter of cylinder 302 is essentially the same as the internal diameter of stent 30. To form valve 300, cylinder 302 is displaced into stent 30, as seen in FIG. 21. Cusp 302' forming, attaching sutures 314 are sewn through cylinder 302 and stent 30 to securely tie cylinder 302 to each cusp 302' support 70, 80, and 90 as seen in FIG. 21. The more superior sutures 316 are cross stitched at apical connections 318 of each cusp 302' support 70, 80, and 90 attachment site and then securely stitched in place along each cusp 302' periphery in a descending and ascending pattern similar to that seen in FIG. 14. The manner of suturing seen in FIG. 21 is used in valves where cusps are formed from tissue such as flattened pericardium derived from living organs and is well known in the art. Also, cylinder 302 may be doubly attached at a second suture line (not shown) similar to suturing line 238 seen in FIG. 14 to provide a guard against eventual dehiscence due to systolic blood flow. The free leaflet surfaces forming each cusp 302' between cusp supports 70, 80, and 90 are preferably made concave so that the leaflet surfaces of each cusp 302' tend to reside in the closed position. The leaflet surfaces of each cusp 302' can be made concave by heat treatment or other material forming methods generally known in the art.

As earlier specified, sutures are preferably GORTEX™ 3-0 suture material; however, other suture material comprising acceptable biochemical inertness and lasting characteristics may be used. As cylinder 302 is attached to stent 30 and as seen in FIG. 21, valve 300 is completely centrally, patently open as in systole. In FIG. 22, valve 300 is rotated and closed such that corresponding sections of superior edge 304 closes upon itself to provide a closed orientation. To reduce pressure loss across valve 300, thin walled GORTEX SURGICAL MEMBRANE™ having a wall thickness of 0.10 mm may be used. While valve 300 is seen to be an aortic valve configuration in FIGS. 21 and 22, the material of cylinder 302 is similarly configured and equally as effectively incorporated into a mitral valve stent 270.

As earlier indicated, each stent 30 and 270 comprises a brim cover 105 and 286, respectively. There are two important reasons for providing a brim cover. First, controlled and limited tissue in-growth at the site of each stent 30 and 270 emplacement allows a balance to be struck the between valve adherence to and valve removability from the annulus into which it is implanted. Second, it is desirable to implant the material of cylinder 330 with antibiotics to decrease the risk of post placement valve infection.

As described earlier, all other parts of each stent 30 and 270 comprise exterior surfaces which are biochemically inert, each brim cover 105 and 286 provides the only surface area whereat adhesion is permitted to occur due to such tissue in-growth. Such tissue in-growth improves adhesion of the grafted valve within the native excised valve orifice. Providing the limited surface area of the brim cover for tissue in-growth also selectively permits a relatively easy excision should valve replacement be necessary.

Figure 17:
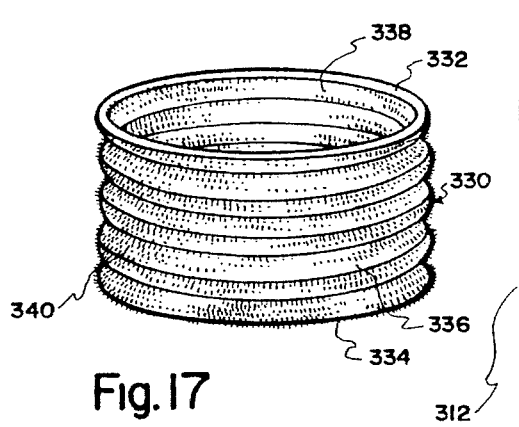
FIG. 17 is a perspective of a cylinder of material used to cover a brim portion of the stent.
Figure 20:
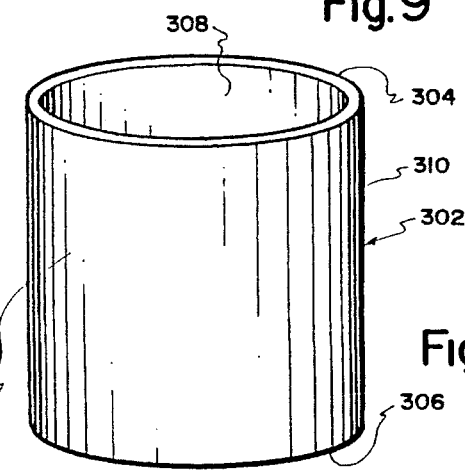
FIG. 20 is a perspective of a cylinder of material from which a trileaflet valve is made.

Each brim cover 105 and 286 is formed from a hollow cylinder 330 of pliant, biocompatible material cut to a length which covers brims of sewing rings 100 and 102 and 276, respectively. A section of such cylinder material is seen in FIG. 17. Cylinder 330 is preferably made of velour dacron a commercially available, medical grade DACRON™, similar to straight knitted dacron a commercially available, medical grade DACRON™, velour available from Bard Implants Division, C. R. Bard, Inc., Concord Road, P.O. Box M, Billerica, Mass. 01821. Velour dacron a commercially available, medical grade DACRON™ is compatible with earlier mentioned antibiotic implantation and tissue in-growth, As seen in FIG. 17, cylinder 330 comprises a free top edge 332, a free bottom edge 234, an exterior surface 336, and an interior surface 338. Disposed between exterior surface 336 and interior surface 338 and between top edge 332 and bottom edge 334 is a plaint, foldable material wall 340. As seen by the section shown in FIG. 18, pliant, foldable wall 340 comprises an inside diameter which distends to the same outside diameter as sewing rings 100 and 102 or alternatively with sewing ring 276 without losing structural integrity.

Figure 18:
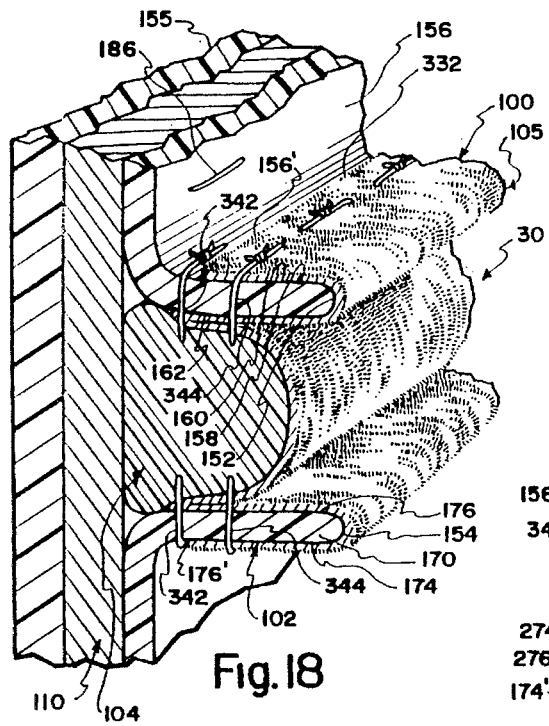
FIG. 18 is an exterior perspective of a medial section of the aortic valve prosthesis stent of FIG. 7 showing the cylinder of material seen in FIG. 17 disposed about and securely affixed to the brim portion of the aortic valve stent.

Preparatory to adding brim cover 105 to stent 30, brims 158 and 170 are securely attached to deformable intermediate interfacing portion 104. As seen in FIG. 18, sutures, generally numbered 342, securely anchor portion 104 between brims 158 and 170. Cylinder 330 is then disposed about sewing rings 100 and 102 such that top edge 332 is foldably disposed in proximity to seamless connection line 156', earlier described of Similarly, free bottom edge 334 is disposed in the proximity of seamless connection line 174'.

Between top edge 322 and bottom edge 334, wall 340 is folded upon itself, in two places, and interposed between interfacing portion 104 and each of the sewing rings 100 and 102 such that interior surface 338 contacts, in seriatum, brim 158 superior surface 160, edge 152, inferior surface 162, the associated exterior surface of interfacing portion 104, and brim 170 superior surface 176, edge 154, and inferior surface 174. So disposed, sutures, generally numbered 344, tightly secure wall 336 to sewing ring 100 and interfacing portion 104 at the top and to sewing ring 102 and interfacing portion 104 at the bottom as seen in FIG. 18.

In similar fashion, sewing ring 276 is covered by another cylinder 330 as seen in FIG. 19. Preparatory to adding brim cover 286 to stent 270, brims 272 and 274 are securely attached to each other. As seen in FIG. 19, sutures, generally numbered 346, affix brim 272 to brim 274. Cylinder 330 is then disposed about sewing ring 276 such that top edge 332 is foldably disposed in proximity to seamless connection line 156'. Similarly, free bottom edge 334 is disposed in the proximity of seamless connection line 174'.

Sutures, generally numbered 348, are affixed to tightly secure wall 336 more medially to brims 158 and 170. Other sutures, generally numbered 350, are disposed radially outwardly from edge 152 to affix wall 336 to brim 170 alone. So disposed wall 336 provides a smooth transition between the otherwise discontinuous connection between edge 152 and superior surface 76 as seen in FIG. 19.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for making a stent for a prosthetic heart valve comprising the steps of:

forming a hollow cylindrical frame comprising raised stanchions and a base for support of a leaflet heart valve;

inserting cylindrically shaped covering into the interior of the hollow cylindrical frame such that each end of the covering extends beyond the stanchions and base of the cylindrical frame;

folding the covering about the cylindrical frame, thereby substantially enveloping the cylindrical frame;

outwardly everting each end of the covering to form at least two sewing rings;

trimming the covering which is disposed between the stanchions such that a pocket is formed about each stanchion;

sewing the trimmed covering to totally enclose each stanchion;

sewing each sewing ring along the line of outward eversion to the cylindrical framed and inserted portion of the covering.

2. The method according to claim 1 wherein the outwardly everting step comprises:

disposing and affixing between said at least two sewing rings a perimetrically variable compliant interfacing portion of soft material.

3. The method according to claim 1 comprising the further step of covering at least one sewing ring with material having tissue ingrowth capability.

* * * * *